United States Patent [19]

Jacobs et al.

[11] Patent Number: 5,290,902
[45] Date of Patent: Mar. 1, 1994

[54] POLYISOCYANATES CONTAINING ALLOPHANATE AND ISOCYANURATE GROUPS, A PROCESS FOR THEIR PRODUCTION FROM CYCLIC DIISOCYANATES AND THEIR USE IN TWO-COMPONENT COATING COMPOSITIONS

[75] Inventors: Patricia B. Jacobs, Pittsburgh; Douglas A. Wicks, Mt. Lebanon, both of Pa.

[73] Assignee: Miles Inc., Pittsburgh, Pa.

[21] Appl. No.: 81,923

[22] Filed: Jun. 22, 1993

[51] Int. Cl.$^5$ .............................. C08G 18/32
[52] U.S. Cl. ...................... 528/49; 528/59; 544/180; 544/193; 544/196; 252/182.21; 252/182.22
[58] Field of Search ............ 528/49, 59; 544/180, 544/193, 196; 252/182.21, 182.22

[56] References Cited

U.S. PATENT DOCUMENTS

| | | | |
|---|---|---|---|
| 3,487,080 | 12/1969 | Matsui et al. | 260/248 |
| 3,996,223 | 12/1976 | Gupta et al. | 260/248 NS |
| 4,324,879 | 4/1982 | Bock et al. | 528/45 |
| 4,412,073 | 10/1983 | Robin | 544/193 |
| 4,582,888 | 4/1986 | Kase et al. | 528/49 |
| 4,604,418 | 8/1986 | Shindo et al. | 524/296 |
| 4,647,623 | 3/1987 | Kase et al. | 525/123 |
| 4,789,705 | 12/1988 | Kase et al. | 524/590 |
| 4,801,663 | 1/1989 | Ueyanagi et al. | 525/528 |
| 5,124,427 | 6/1992 | Potter et al. | 528/67 |

FOREIGN PATENT DOCUMENTS 61-151179 7/1986 Japan .

Primary Examiner—Maurice J. Welsh
Attorney, Agent, or Firm—Joseph C. Gil; Thomas W. Roy

[57] ABSTRACT

The present invention is directed to a polyisocyanate mixture which
i) has an NCO content of 5 to 47% by weight,
ii) is prepared from an isocyanate component substantially containing one or more cyclic organic diisocyanates having (cyclo)aliphatically-bound isocyanate groups and
iii) contains isocyanurate and allophanate groups in a molar ratio of monoIsocyanurates to monoallophanates of 10:1 to 1:10, wherein the allophanate groups are formed from urethane groups which are based on the reaction product of an organic diisocyanate having (cyclo)aliphatically bound isocyanate groups and a monoalcohol containing at least 1 carbon atom and having a molecular weight of up to 2500.

The present invention is also directed to a process for the production of these polyisocyan mixtures and to their use, optionally in blocked form, as an isocyanate component in two-component coating compositions.

13 Claims, No Drawings

POLYISOCYANATES CONTAINING ALLOPHANATE AND ISOCYANURATE GROUPS, A PROCESS FOR THEIR PRODUCTION FROM CYCLIC DIISOCYANATES AND THEIR USE IN TWO-COMPONENT COATING COMPOSITIONS

BACKGROUND OF THE INVENTION

The present invention is directed to polyisocyanates which contain allophanate groups and isocyanurate groups and are prepared from cyclic diisocyanates containing (cyclo)aliphatically bound isocyanate groups. The present invention is also directed to a process for the production of these polyisocyanates and to their use in two-component coating compositions.

Polyisocyanates containing isocyanurate groups are known and disclosed in U.S. Pat. Nos. 3,487,080, 3,996,223, 4,324,879 and 4,412,073. While these polyisocyanates possess many outstanding properties, they do require improvement. First, the viscosity of commercially available polyisocyanates containing isocyanurate groups needs to be reduced in order to reduce the amount of solvent which is necessary to obtain a suitable processing viscosity. Presently, there are an increasing number of government regulations which limit the amount of volatile solvents which may be present in coating systems. Therefore, isocyanurate group-containing polyisocyanates may be precluded from certain applications because it is not possible to reduce the viscosity of these polyisocyanates to a suitable processing viscosity without using high amounts of solvent. Second, in reducing the viscosity of the coating compositions, it is important that the other properties of the coatings, such as hardness and solvent resistance, remain at high levels.

It has been proposed in U.S. Pat. 4,801,663 to reduce the viscosity of isocyanurate group-containing polyisocyanates prepared from 1,6-hexamethylene diisocyanate (HDI). By terminating the reaction at a very low degree of trimerization higher contents of the monoisocyanurate of HDI are obtained and the quantity of polyisocyanates containing more than one isocyanurate ring is reduced. Because these latter polyisocyanates have a much higher viscosity than the monoisocyanurate, the resulting polyisocyanates have a reduced viscosity. However, a significant disadvantage of this system is that because the reaction is terminated at a very low degree of trimerization, the overall yield is very low and the amount of HDI which must be separated from the product is substantially increased. In other words the small reduction in viscosity is offset by a significant increase in the production cost of the product. Further, the resulting product does not possess optimum compatibility with highly branched polyester resins.

Accordingly, it is an object of the present invention to provide polyisocyanates which have a reduced solution viscosity and and yet retain the performance properties of the corresponding higher viscosity polyisocyanates which do not contain allophanate groups. It is an additional object of the present invention to provide polyisocyanates which may be produced at reasonable production costs and which are obtained in high yields. Surprisingly, these objectives may be achieved in accordance with the present invention as described hereinafter by the incorporation of specific monoalcohols before or during the trimerization of cyclic diisocyanates containing (cyclo)aliphatically bound isocyanate groups to produce a polyisocyanate containing isocyanurate and allophanate groups.

U.S. Pat. Nos. 4,582,888, 4,604,418, 4,647,623, 4,789,705 are directed the incorporation of various diols in order to improve the compatibility of the resulting polyisocyanates with certain solvents and co-reactants. While the use of diols may improve the compatibility of the polyisocyanates, the diols do not reduce the viscosity of the polyisocyanurates for a given yield.

Many of these references as well as those previously set forth disclose the use of monoalcohols or glycols as co-catalysts for the trimerization reaction. However, none of these references suggest the incorporation of allophanate groups to reduce the viscosity of polyisocyanates containing isocyanurate groups. Further, these references teach that the use of these co-catalysts should be kept to a minimum since the resulting urethane groups adversely affect the drying time of coatings prepared from the polyisocyanates. In particular, U.S. Pat. No. 4,582,888 cautions against the use of any amount of monoalcohol which is in excess of that needed to dissolve the catalyst.

Japanese Publication 61-151179 discloses the use of monoalcohols containing 6 to 9 carbon atoms as co-catalysts for trimerization catalysts which do not trimerize HDI in the absence of a co-catalyst.

It has been disclosed in U.S. Pat. No. 5,124,427 and in copending applications, U.S. Ser. Nos. 07/890,979 and 07/891,535, to conduct the trimerization of organic diisocyanates in the presence of monoalcohols having molecular weights of up to 2500 to incorporate allophanate groups into the final products and reduce their viscosity. It has also been disclosed in copending application, U.S. Ser. No. 07/897,732, to use mixtures of 1,6-hexamethylene diisocyanate and diisocyanates having (cyclo)aliphatically-bound isocyanate groups as starting materials to prepare polyisocyanates which may be formulated to provide coatings with improved dry times and good environmental etch resistance.

Even though these applications disclose the use of diisocyanates having (cyclo)aliphatically-bound isocyanate groups as starting materials, they do not recognize the unexpected advantages described hereinafter which may be obtained by using cyclic organic diisocyanates having (cyclo)aliphatically-bound isocyanate groups as starting materials.

SUMMARY OF THE INVENTION

The present invention is directed to a polyisocyanate mixture which
i) has an NCO content of 5 to 47% by weight,
ii) is prepared from an isocyanate component substantially containing one or more cyclic organic diisocyanates having (cyclo)aliphatically-bound isocyanate groups and
iii) contains isocyanurate and allophanate groups in a molar ratio of monoisocyanurates to monoallophanates of 10:1 to 1:10, wherein the allophanate groups are formed from urethane groups which are based on the reaction product of an organic diisocyanate having (cyclo)aliphatically bound isocyanate groups and a monoalcohol containing at least 1 carbon atom and having a molecular weight of up to 2500.

The present invention is also directed to a process for the production of a polyisocyanate mixture having an NCO content of 5 to 47% by weight and containing isocyanurate and allophanate groups in a molar ratio of monoisocyanurates to monoallophanates of 10:1 to 1:10 by
a) catalytically trimerizing a portion of the isocyanate groups of an isocyanate component substantially containing one or more cyclic organic diisocyanates having (cyclo)aliphatically bound isocyanate groups,
b) adding 0.01 to 0.5 moles, per mole of organic diisocyanate, of a monoalcohol containing at least one carbon atom and having a molecular weight of up to 2500 to the organic diisocyanate prior to or during the trimerization reaction of step a) and
c) terminating the trimerization reaction at the desired degree of trimerization by adding a catalyst poison and/or by thermally deactivating the catalyst.

Finally, the present invention is directed to the use of these polyisocyanate mixtures, optionally in blocked form, as an isocyanate component in two-component coating compositions.

DETAILED DESCRIPTION OF THE INVENTION

In accordance with the present invention the term "monoisocyanurate" means a polyisocyanate containing one isocyanurate group and formed from three diisocyanate molecules, and the term "polyisocyanurate" means a polyisol cyanate containing more than one isocyanurate group. The term "monoallophanate" means a polyisocyanate containing one allophanate group and formed from two diisocyanate molecules and 1 monoalcohol molecule, and the term "polyallophanate" means a polyisocyanate containing more than one allophanate group. The term "(cyclo)aliphatically bound isocyanate groups" means aliphatically and/or cycloaliphatically bound isocyanate groups.

In accordance with the present invention one or more cyclic organic diisocyanates having (cyclo)aliphatically-bound isocyanate groups are used as the starting material for the trimerization/allophantization reaction. While it is possible to use minor quantities of non-cyclic diisocyanates, the starting mixture substantially contains cyclic diisocyanates, i.e., greater than 90%, preferably greater than 95% and more preferably 100%, based on the weight of the starting mixture.

Examples of cyclic diisocyanates having (cyclo)aliphatically-bound isocyanate groups include cyclohexane-1,3-and -1,4-diisocyanate, 1-isocyanato-2-isocyanatomethyl cyclopentane, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)methane, xylylene diisocyanate, $\alpha,\alpha,\alpha',\alpha'$-tetramethyl-1,3-and/or -1,4-xylylene diisocyanate, 1-isocyanato-1-methyl-4(3)-isocyanatomethyl cyclohexane, and 2,4- and/or 2,6-hexahydrotoluylene diisocyanate. Mixtures of cyclic diisocyanates may also be used. Preferred cyclic diisocyanates are isophorone diisocyanate and bis-(4-isocyanatocyclohexyl)-methane; isophorone diisocyanate is especially preferred.

It is also possible in accordance with the present invention to use blends of the previously mentioned diisocyanates with monoisocyanates or polyisocyanates having 3 or more isocyanate groups, provided that the isocyanate groups are (cyclo)aliphatically bound.

In accordance with the present invention it is preferred to treat the starting diisocyanates by bubbling an inert gas such as nitrogen through the starting diisocyanate in order to reduce the content of carbon dioxide. This process is discussed in German Offenlegungsschrift 3,806,276 (U.S. application, Ser. No. 07/311,920).

Trimerization catalysts which are suitable for the process according to the invention include those previously known such as alkali phenolates of the type described in GB-PS 1,391,066 or GB-PS 1,386,399; aziridine derivatives in combination with tertiary amines of the type described in U.S. Pat. No. 3,919,218; quaternary ammonium carboxylates of the type described in U.S. Pat. Nos. 4,454,317 and 4,801,663; quaternary ammonium phenolates with a zwitterionic structure of the type described in U.S. Pat. No. 4,335,219; ammonium phosphonates and phosphates of the type described in U.S. Pat. No. 4,499,253; alkali carboxylates of the type described in DE-OS 3,219,608; basic alkali metal salts complexed with acyclic organic compounds as described in U.S. Pat. No. 4,379,905 such as potassium acetate complexed with a polyethylene glycol which contains an average of 5 to 8 ethylene oxide units; basic alkali metal salts complexed with crown ethers as described in U.S. Pat. No. 4,487,928; aminosilyl group-containing compounds such as aminosilanes, diaminosilanes, silylureas and silazanes as described in U.S. Pat. No. 4,412,073; and mixtures of alkali metal fluorides and quaternary ammonium or phosphonium salts as described in U.S. Ser. No. 07/391,213. The trimerization catalysts should also catalyze the formation of allophanate groups from urethane groups.

Phosphines, such as those described in DE-OS 1,935,763, are not suitable for preparing the products of the present invention. The phosphines, in addition to promoting the trimerization reaction, also promote the dimerization of diisocyanates. Also not suitable are Mannich bases, for example, those based on nonylphenol, formaldehyde and dimethylamine of the type described in U.S. Pat. Nos. 3,996,223 and 4,115,373.

Particularly suitable as catalysts for the process according to the invention are quaternary ammonium hydroxides corresponding to the formula

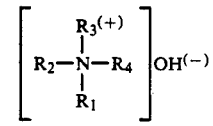

as described in U.S. Pat. No. 4,324,879 and German Offenlegungsschriften 2,806,731 and 2,901,479. Preferred quaternary ammonium hydroxides are those wherein the radicals $R_1$ to $R_4$ represent identical or different alkyl groups having from 1 to 20, preferably from 1 to 4 carbon atoms, which may optionally be substituted by hydroxyl groups. Two of the radicals $R_1$ to $R_4$ may form a heterocyclic ring having from 3 to 5 carbon atoms together with the nitrogen atom and optionally with a further nitrogen or oxygen atom. Also the radicals $R_1$ to $R_3$ in each case may represent ethylene radicals which form a bicyclic triethylene diamine structure together with the quaternary nitrogen atom and a further tertiary nitrogen atom, provided that the radical $R_4$ then represents a hydroxyalkyl group having from 2 to 4 carbon atoms in which the hydroxyl group is preferably arranged in a 2-position to the quaternary nitrogen atom. The hydroxyl-substituted radical or the hydroxyl-substituted radicals may also contain other substituents, particularly $C_1$ to $C_4$- alkoxy substituents.

The production of these quaternary ammonium catalysts takes place in known manner by reacting a tertiary amine with an alkylene oxide in an aqueous-alcoholic medium (c.f. U.S. Pat. No. 3,995,997, col. 2, lines 19-44). Examples of suitable tertiary amines include trimethylamine, tributylamine, 2-dimethylaminoethanol, triethanolamine, dodecyldimethylamine, N,N-dimethylcyclohexylamine, N-methylpyrrolidine, N-methylmorpholine and 1,4-diazabicyclo-[2,2,2]-octane. Examples of suitable alkylene oxides include ethylene oxide, propylene oxide, 1,2-butylene oxide, styrene oxide and methoxy, ethoxy or phenoxy propylene oxide. The most preferred catalysts from this group are N,N,N-trimethyl-N-(2-hydroxyethyl)-ammonium hydroxide and N,N,N-trimethyl-N-(2-hydroxypropyl)ammonium hydroxide. Another most preferred catalyst is N,N,N-trimethyl-N-benzyl-ammonium hydroxide.

The trimerization of the starting diisocyanate mixture may be carried out in the absence or in the presence of solvents which are inert to isocyanate groups. Depending on the area of application of the products according to the invention, low to medium-boiling solvents or high-boiling solvents can be used. Suitable solvents include esters such as ethyl acetate or butyl acetate; ketones such as acetone or butanone; aromatic compounds such as toluene or xylene; halogenated hydrocarbons such as methylene chloride and trichloroethylene; ethers such as diisopropylether; and alkanes such as cyclohexane, petroleum ether or ligroin.

The trimerization catalysts are generally used in quantities of about 0.0005 to 5% by weight, preferably about 0.001 to 2% by weight, based on the diisocyanate used. If, for example, a preferred catalyst such as N,N,N-trimethyl-N-(2-hydroxypropyl)-ammonium hydroxide is used, then quantities of about 0.0005 to 1% by weight, preferably about 0.001 to 0.1 by weight, based on starting diisocyanate, are generally sufficient. The catalysts may be used in pure form or in solution. The previously named solvents which are inert to isocyanate groups are suitable as solvents, depending on the type of catalysts. Dimethyl formamide and dimethyl sulphoxide may also be used as solvents for the catalysts. Also suitable are monoalcohols such as methanol, butanol or 2-ethyl hexanol.

The simultaneous use of co-catalysts is possible in the process according to the invention, but not necessary. All substances from which a polymerizing effect on isocyanates is known are suitable as co-catalysts such as those described in DE-OS 2,806,731. The co-catalysts are optionally used in a lesser amount on a weight basis in relation to the amount of the trimerization catalyst.

In accordance with the present invention urethane groups and subsequently allophanate groups are incorporated into the polyisocyanates by the use of aliphatic, cycloaliphatic, araliphatic or aromatic monoalcohols. The monoalcohols may be linear, branched or cyclic, contain at least one carbon atom and have a molecular weight of up to 2500. The monoalcohols may optionally contain other hetero atoms in the form of, e.g., ether groups. The molar ratio of monoalcohol to diisocyanate is about 0.01 to 0.5, preferably about 0.04 to 0.2. Preferred monoalcohols are hydrocarbon monoalcohols and monoalcohols containing ether groups.

The hydrocarbon monoalcohols preferably contain 1 to 36, more preferably 1 to 20 and most preferably 1 to 8 carbon atoms. Examples of suitable monoalcohols include methanol, ethanol, n-propanol, isopropanol, n-butanol, isobutanol and tert. butanol, n-pentanol, 2-hydroxy pentane, 3-hydroxy pentane, the isomeric methyl butyl alcohols, the isomeric dimethyl propyl alcohols, neopentyl alcohol, n-hexanol, n-heptanol, n-octanol, n-nonanol, 2-ethyl hexanol, trimethyl hexanol, cyclohexanol benzyl alcohol, phenol, the cresols, the xylenols, the trimethylphenols, decanol, dodecanol, tetradecanol, hexadecanol, octadecanol, 2,6,8-trimethylnonanol, 2-t-butyl-cyclohexanol, 4-cyclohexyl-l-butanol, 2,4,6,-trimethyl benzyl alcohol, branched chain primary alcohols and mixtures thereof (which are available from Henkel under to Standamul trademark) and mixtures of linear primary alcohols (which are available from Shell under the Neodol trademark).

Preferred ether-containing monoalcohols include ethoxy methanol, methoxy ethanol, ethoxy ethanol, the isomeric methoxy or ethoxy propanols, the isomeric propoxy methanols and ethanols, the isomeric methoxy butanols, the isomeric butoxy methanols, furfuralcohol and other monoalcohols which have a molecular weight of up to 2500 and are based on ethylene oxide, propylene oxide and/or butylene oxide.

It is also possible in accordance with the present invention to use mixtures of the previously described monoalcohols.

When the polyisocyanates containing isocyanurate groups and allophanate groups accordingly to the invention are prepared from monoalcohols containing ethylene oxide units, the polyisocyanates may be dispersed in water as described in U.S. Pat. No. 5,200,489, the disclosure of which is herein incorporated by reference.

The reaction temperature for isocyanurate and allophanate formation in accordance with the present invention is about 10 to 160° C., preferably about 50 to 150° C. and more preferably about 70 to 120° C.

The process according to the invention may take place either batchwise or continuously, for example, as described below. The starting diisocyanate is introduced with the exclusion of moisture and optionally with an inert gas into a suitable stirred vessel or tube and optionally mixed with a solvent which is inert to isocyanate groups such as toluene, butyl acetate, diisopropylether or cyclohexane. The previously described monoalcohol may be introduced into the reaction vessel in accordance with several embodiments. The monoalcohol may be prereacted with either or both of the components of the starting diisocyanate mixture to form urethane groups prior to introducing the diisocyanates into the reaction vessel; the monoalcohol may be mixed with the diisocyanates and introduced into the reaction vessel; the monoalcohol may be separately added to the reaction vessel either before or after, preferably after, the diisocyanates are added; or the catalyst may be dissolved in the monoalcohol prior to introducing the solution into the reaction vessel.

The polyisocyanates according to the invention may also be prepared by blending polyisocyanates containing isocyanurate groups with monoallophonates.

At a temperature of about 60° C. and in the presence of the required catalyst or catalyst solution the trimerization begins and is indicated by an exothermic reaction. As the reaction temperature increases the conversion rate of urethane groups to allophanate groups increases faster than the formation of isocyanurate groups. Accordingly, at some temperature for a given degree of trimerization, the urethane groups are substantially converted to allophanate groups, while at some lower temperature unreacted urethane groups remain. The progress of the reaction is followed by determining the NCO content by a suitable method such as titration, refractive index or IR analysis. Thus, the reaction may be terminated at the desired degree of trimerization. The termination of the trimerization reaction can take place, for example, at an NCO content of about 10% to 47%, preferably about 15 to 40%.

The termination of the trimerization reaction can take place, for example, by the addition of a catalyst-poison of the type named by way of example in the above-mentioned literature references. For example, when using basic catalysts the reaction is terminated by the addition of a quantity, which is at least equivalent to the catalyst quantity, of an acid chloride such as benzoyl chloride. When using heat-labile catalysts, for example, the previously described quaternary ammonium hydroxides, poisoning of the catalyst by the addition of a catalyst-poison may be dispensed with, since these catalysts decompose in the course of the reaction. When using such catalysts, the catalyst quantity and the reaction temperature are preferably selected such that the catalyst which continuously decomposes is totally decomposed when the desired degree of trimerization is reached. The quantity of catalyst or reaction temperature which is necessary to achieve this decomposition can be determined by a preliminary experiment. It is also possible initially to use a lesser quantity of a heat sensitive catalyst than is necessary to achieve the desired degree of trimerization and to subsequently catalyze the reaction by a further incremental addition of catalyst, whereby the quantity of catalyst added later is calculated such that when the desired degree of trimerization is achieved, the total quantity of catalyst is spent. The use of suspended catalysts is also possible. These catalysts are removed after achieving the desired degree of trimerization by filtering the reaction mixture.

The working-up of the reaction mixture, optionally after previous separation of insoluble catalyst constituents, may take place in various ways depending upon how the reaction was conducted and the area of application for the isocyanates. It is possible to use the polyisocyanates according to the invention which have been produced in solution directly as a lacquer raw material, without a purification stage, if it is not necessary to reduce the free monomer content. Any solvent used during trimerization reaction and any unreacted monomer present in the polyisocyanate product can also be removed by distillation in known manner. The product obtained after distillation generally contains a total of less than 2, preferably less than 1% of free (unreacted) monomeric diisocyanates. The products according to the invention generally range from viscous liquids to solids.

The solid products according to the present invention have a lower solution viscosity than similar products which do not contain allophanate groups. In other words the products according to the invention may be dissolved and the viscosity reduced to a suitable processing viscosity using less solvent than is necessary for similar solid products which do not contain allophanate groups. Also, certain products according to the invention have lower formulation viscosities than liquid polyisocyanates containing isocyanurate groups prepared from non-cyclic diisocyanates, but which do not contain allophanate groups.

The products according to the present invention are polyisocyanates containing isocyanurate groups and allophanate groups. The products may also contain residual urethane groups which have not been converted to allophanate groups depending upon the temperature maintained during the reaction and the degree of isocyanate group consumption. The ratio of monoisocyanurate groups to monoallophanate groups present in the polyisocyanates according to the invention is about 10:1 to 1:10, preferably about 5:1 to 1:7. These values may be determined by gel permeation chromatography (GPC) by determining the areas under the peaks for the monoisocyanurate and monoallophanate groups.

The products according to the invention are valuable starting materials for the production of polyisocyanate polyaddition products by reaction with compounds containing at least two isocyanate reactive groups. Preferred products are one or two-component polyurethane coatings.

Prior to their use in coating compositions, the polyisocyanate mixtures according to the invention may be blended with other known polyisocyanates, e.g., polyisocyanate adducts containing bioret, isocyanurate, allophanate, urethane, urea, carbodiimide, and/or uretdione groups. The resulting mixtures will generally have a reduced viscosity due to the effect of the polyisocyanates according to the invention. These mixtures contain at least 20%, preferably at least 50%, of the polyisocyanates according to the invention, based on the total weight of the polyisocyanate component.

Preferred reaction partners for the products according to the invention, which may optionally be present in blocked form, are the polyhydroxy polyesters, polyhydroxy polyethers, polyhydroxy polyacrylates, polyhydroxy polylactones, polyhydroxy polyurethanes, polyhydroxy polyepoxides and optionally low molecular weight, polyhydric alcohols known from polyurethane coatings technology. Polyamines, particularly in blocked form, for example as polyketimines or oxazolidines are also suitable reaction partners for the products according to the invention. Also suitable are polyaspartic acid derivatives (succinates) containing secondary amino groups, which also function as reactive diluents.

The amounts of the polyisocyanates according to the invention and their reaction partners are selected to provide equivalent ratio of isocyanate groups (whether present in blocked or unblocked form) to isocyanate-reactive groups of about 0.8 to 3, preferably about 0.9 to 1.5.

To accelerate hardening, the coating compositions may contain known polyurethane catalysts, e.g., tertiary amines such as triethylamine, pyridine, methyl pyridine, benzyl dimethylamine, N,N-dimethylamino cyclohexane, N-methylpiperidine, pentamethyl diethylene triamine, 1,4-diazabicyclo[2,2,2]-octane and N,N'-dimethyl piperazine; or metal salts such as iron(III)-chloride, zinc chloride, zinc-2-ethyl caproate, tin(II)-ethyl caproate, dibutyltin(IV)-dilaurate and molybdenum glycolate.

The products according to the invention are also valuable starting materials for two-component polyurethane stoving enamels in which the isocyanate groups are used in a form blocked by known blocking agents. The blocking reaction is carried out in known manner by reacting the isocyanate groups with suitable blocking agents, preferably at an elevated temperature (e.g. about 40 to 160° C.), and optionally in the presence of a suitable catalyst, for example, the previously described tertiary amines or metal salts.

Suitable blocking agents include monophenols such as phenol, the cresols, the trimethylphenols and the tert. butyl phenols; tertiary alcohols such as tert. butanol, tert. amyl alcohol and dimethylphenyl carbinol; compounds which easily form enols such as acetoacetic ester, acetyl acetone and malonic acid derivatives, e.g. malonic acid diethylester; secondary aromatic amines such as N-methyl aniline, the N-methyl toluidine, N-phenyl toluidine and N-phenyl xylidine; imides such as succinimide; lactams such as $\epsilon$-caprolactam and $\delta$-valerolactam; oximes such as butanone oxime, methyl amyl ketoxime and cyclohexanone oxime; mercaptans such as methyl mercaptan, ethyl mercaptan, butyl mercaptan, 2-mercaptobenzthiazole, $\alpha$-naphthyl mercaptan and dodecyl mercaptan; and triazoles such as 1H-1,2,4-triazole.

The coating compositions may also contain other additives such as pigments, dyes, fillers, levelling agents and solvents. The coating compositions may be applied to the substrate to be coated in solution or from the melt by conventional methods such as painting, rolling, pouring or spraying.

The coating compositions containing the polyisocyanates according to the invention provide coatings which have improved dry times, adhere surprisingly well to a metallic base, and are particularly light-fast, color-stable in the presence of heat and very resistant to abrasion. Furthermore, they are characterized by high hardness, elasticity, very good resistance to chemicals, high gloss, good weather resistance, good environmental etch resistance and good pigmenting qualities. The polyisocyanates according to the invention also possess good compatibility with highly branched polyester resins.

The invention is further illustrated, but is not intended to be limited by the following examples in which all parts and percentages are by weight unless otherwise specified.

EXAMPLES

Polyisocyanate 1—According to the invention

To a 2 liter 3-neck flask equipped with a gas bubbler, mechanical stirrer, thermocouple and condenser, were added 1110 grams of isophorone diisocyanate and 68 grams of n-butanol. The stirred mixture was heated for 2 hours at 70° C. while dry nitrogen was bubbled through the reaction mixture. The temperature of the urethane reaction mixture was then raised to 80° C. To the reaction mixture at 80° C. were added dropwise 10.84 grams (300 ppm) of a catalyst solution, which was prepared by reducing a 40% solution of benzyltrimethyl ammonium hydroxide in methanol to a solids content of 5% by the addition of n-butanol. When the reaction mixture attained an NCO content of 25.90%, the reaction was stopped by adding 2.6 grams of a 25% solution of di-(2-ethylhexyl)-phosphate (586 ppm) in hexamethylene diisocyanate. The excess monomer was removed by thin film evaporation to provide a pale yellow solid having a viscosity of 7667 mPa.s at 80° C., an NCO content of 14.2% and a free monomer (IPDI) content of 0.29%. The actual yield was 42.4% and the molar ratio of monoisocyanurate to monoallophanate was 1:4.8.

Polyisocyanates 2-6—According to the invention

Polyisocyanates 2-6 were prepared in a manner analogous to Polyisocyanate 1 using the parameters set forth in Table 1. The properties of the stripped products are set forth in Table 2.

TABLE 1

| Polyisocyanate | Formulation (parts) | Reaction Temp. | Catalyst (ppm) | Final % NCO Reaction Mixture |
|---|---|---|---|---|
| 2 | 100 IPDI 7.0 n-BuOH | 82 | 487 | 29.4 |
| 3 | 100 IPDI 4.6 n-BuOH | 78 | 351 | 30.8 |
| 4 | 100 IPDI 4.8 n-BuOH | 85 | 459 | 27.3 |
| 5 | 100 IPDI 4.9 n-BuOH | 85 | 524 | 23.1 |
| 6 | 100 IPDI 6.8 n-BuOH | 85 | 361 | 22.4 |

TABLE 2

| Polyisocyanate | % NCO | Viscosity at 80° C. | % Free Monomer | % Yield | Molar ratio of Monoisocyanurate to Monoallophanate |
|---|---|---|---|---|---|
| 2 | 13.8 | 1819 | 1.3 | 17.5 | 1:6.7 |
| 3 | 14.8 | 3441 | 0.12 | 22.1 | 1:6.1 |
| 4 | 15 | 673,240 | 0.09 | 41.5 | 1:1.9 |
| 5 | 13.3 | semi-solid | 0.33 | 42.3 | 1.7:1 |
| 6 | 13.6 | semi-solid | 0.15 | 58.2 | 1:1.3 |

Polyisocyanate 7—According to the invention

To a 2 liter 3-neck flask equipped with a gas bubbler, mechanical stirrer, thermocouple and condenser, were added 1000 grams of bis-(4-isocyanatocyclohexyl)-methane and 37.15 grams of n-butanol. The stirred mixture was heated for 2 hours at 85° C. while dry nitrogen was bubbled through the reaction mixture. To the reaction mixture at 85° C. were added dropwise 3.0 grams (150 ppm) of the catalyst solution used for the preparation of Polyisocyanate 1. When the reaction mixture reached an NCO content of 25.0%, the reaction was stopped by adding 1.2 grams of a 25% solution of di-(2-ethylhexyl)-phosphate (300 ppm) in hexamethylene diisocyanate. The excess monomer was removed by thin film evaporation to provide a pale yellow solid having an NCO content of 12.5% and a free monomer content of 0.85%. The yield was 23% and the molar ratio of monoisocyanurate to monoallophanate was 1:2. In the example the monourethanes which were not converted to allophanates were removed during thin film evaporation.

Polyisocyanate 8—Comparison

To a 2 liter 3-neck flask equipped with a gas bubbler, mechanical stirrer, thermocouple and condenser, were added 1000 grams of bis-(4-isocyanatocyclohexyl)-methane. The stirred diisocyanate was heated for 30 minutes at 70° C. while dry nitrogen was bubbled through it. To the diisocyanate at 70° C. was added dropwise 1.0 gram (176 ppm) of the catalyst solution. The catalyst solution was prepared by mixing 23.6 grams of a 40% benzyltrimethylammonium hydroxide solution in methanol with 29.95 grams of 1-butanol. After approximately 1 hour, the reaction mixture reached an NCO content of 27.85%. The reaction was stopped by adding 0.38 grams of di-(2-ethylhexyl)-phosphate (300 ppm) in hexamethylene diisocyanate. The excess monomer was removed by thin film evaporation to provide a pale yellow solid having an NCO content of 14.8% and a free monomer content of 1.85%. The yield was 21%.

Polyisocyanate 9—Comparison

An isocyanurate group-containing polyisocyanate prepared by trimerizing a portion of the isocyanate groups of 1,6-hexamethylene diisocyanate and having an isocyanate content of 21.6% by weight, a content of monomeric diisocyanate of <0.2%, a viscosity at 20° C. of 3000 mPa.s (Desmodur N-3300, available from Miles).

Polyisocyanate 10—Comparison

An isocyanurate group-containing polyisocyanate present as a 70% solution in a mixture of aromatic hydrocarbons (Aromatic 100 solvent, available from Exxon) and prepared by trimerizing a portion of the isocyanate groups of isophorone diisocyanate, wherein the solution has an isocyanate content of 11.7% by weight, a content of monomeric diisocyanate of <0.5%, a viscosity at 23° C. of 1500 to 3500 mPa.s (Desmodur Z-4370/2, available from Miles.

Polyisocyanate 11—Comparison

To a 500 ml 3-neck flask equipped with a gas bubbler, mechanical stirrer, thermometer and condenser were added 301.7 grams of hexamethylene diisocyanate and 13.3 grams of 1-butanol. Dry nitrogen was bubbled through the stirred reaction mixture while it was heated at 60° C. When the urethane reaction was complete (about 1 hour), the temperature was raised to 90° C. To the reaction mixture at 90° C. were added 0.214 parts of a 4.4% solution of trimethylbenzylammonium hydroxide dissolved in 1-butanol. The reaction temperature was maintained at 90 to 100° C. When the reaction mixture reached NCO contents of 40.1% and 37.0%, an additional 0.12 parts of the catalyst solution was added. When the reaction mixture reached an NCO content of 34.8%, the reaction was stopped by adding 0.214 parts of di-(2-ethylhexyl) phosphate. The excess monomer was removed by thin film evaporation to provide an almost colorless, clear liquid having a viscosity of 630 mPa.s (25° C.), an NCO content of 19.7%, and a free monomer (HDI) content of 0.35%. The yield was 48.6%. The yield was calculated by determining the percentage of free hexamethylene diisocyanate in the product prior to distillation.

Polyol 1

A polyester polyol having an OH equivalent weight of 740, an OH content of 2.3% and a functionality of about 5, present as a 70%. solution in butyl acetate and prepared from 20.3 parts of a fatty acid mixture (Prifac 7990, available from Unichema International), 14.9 parts trimethylol propane, 15.5 parts pentaerythritol, 20.3 parts benzoic acid, 1.6 parts maleic anhydride and 27.5 parts phthalic anhydride.

Polyol 2

A polyacrylate polyol having an OH equivalent weight of 357, an OH content of 4.7% and an acid number of <20, present as a 75% solution in xylene, and prepared from 9.27% styrene, 53.95% hydroxypropyl methacrylate, 27.6% butyl acrylate and 1.85% acrylic acid, using 7.33% di-tert-butyl peroxide as initiator.

Additive 1

A hindered amine light stabilizer (available as Tinuvin 292 from Ciba-Geigy).

Additive 2

A benzotriazole light stabilizer (available as Tinuvin 384 from Ciba-Geigy).

Additive 3

An acrylate copolymer (available as Byk 358 from Byk Chemie).

EXAMPLE 1

The viscosity of Polyisocyanates 1-5 and Comparison Polyisocyanate 10 were measured at 100% solids using a Brookfield cone and plate viscometer and at various solids contents after the addition of Aromatic 100 solvent (available from Exxon) using a heated Brookfield spindle viscometer. The results are set forth in Table 3.

TABLE 3

| Polyisocyanate | Viscosity (m.Pas) | | | | |
|---|---|---|---|---|---|
| | 100% Solids (80° C.) | 70% Solids | 60% Solids | 50% Solids | 40% Solids |
| 10 (Comp) | — | 4400 | 170 | 26 | 10 |
| 2 | 1800 | 83 | 23 | 11 | — |
| 4 | 63000 | 190 | 35 | 15 | — |
| 3 | 3400 | 93 | 25 | 13 | — |
| 1 | 7700 | 125 | 29 | 13 | — |
| 5 | solid | — | 88 | 22 | 10 |
| 7 | — | 2260 | — | — | — |
| 8 (Comp) | — | 6400 | — | — | — |

Table 3 demonstrates that the solution viscosities obtained from the polyisocyanates containing isocyanurate groups and allophanate groups according to the invention are significantly lower than those obtained from Comparison Polyisocyanate 10 which contained isocyanurate groups, but did not contain allophanate groups. Table 3 also demonstrates that 1) as the amount of alcohol used to prepare the polyisocyanate increases, the viscosity decreases and 2) higher conversion levels (lower NCO contents when the reaction is terminated) lead to higher viscosities.

Example 2-9—Ambient cure coating compositions

Clear coating compositions were prepared from Polyol 1 and Polyisocyanate 1 as well as Comparison Polyisocyanates 9-11 as set forth in Table 4. The compositions were formulated at an NCO/OH equivalent ratio of 1.1:1.0. The compositions also contained a catalyst, i.e., dibutyltin dilaurate (available as Metacure T-12 from Air Products and Chemicals), which was present as a 10% solution in butyl acetate. The coating compositions were reduced using a 2/1/1 solvent blend of methyl ethyl ketone, methyl isobutyl ketone and Exxate 600 solvent (available from Exxon). All of the coating compositions were formulated at the same solids content. The percentages of the polyisocyanate mixtures set forth in Examples 6-9 are based on solids.

The properties of the resulting coatings are set forth in Table 5. The viscosity was determined at 25° C. using a #2 Zahn cup. The tack free time was determined by placing a cotton ball on the film at various intervals until no fibers adhered to the film. The hardness of the coatings was determined in accordance with ASTM D4366-87 (Koenig Pendulum Hardness).

The Gardner dry time was determined using a Gardner Circular Drying Time Recorder.

Set-to-touch—During the first stage of drying the film is mobile and partially flows back into the scribed channel. The film may be considered "set-to-touch" when it no longer flows back and the stylus begins to leave a clear channel.

Surface-dry—when sytlus no longer leaves clear channel, but begins to rupture the dry upper layer of the curing film, the film is considered to be "surface-dry."

Hard-dry—when the stylus no longer ruptures the film, but moves freely upon the surface, the cross-section of the film may be considered to have reached the "hard-dry" condition.

Mar-free—When the stylus no longer mars the surface of the film at all the film may be considered to be "mar-free."

tween the coating compositions of Examples 4 and 5 is an order of magnitude greater than the viscosity difference between Examples 2 and 3.

In terms of drying time, the allophanate-containing coating composition of Example 5 is slower than the one from Example 4 which did not contain allophanate groups. The same trend is present when comparing the coating compositions containing polyisocyanates prepared from HDI in Examples 2 and 3. It is important to note that the allophanate-containing coating composition of Example 5 had a faster tack free time than the one from Example 2. The tack free time is important because it is an indication of how fast the coating stops picking up dust and, thus, how fast it can be removed from the spray hood.

The presence of allophanate groups appeared to retard the development of hardness; however, in fully cured films (2 week ambient cure), the hardnesses of the

TABLE 4

| | Example | | | | | | | |
|---|---|---|---|---|---|---|---|---|
| | 2 (Comp) | 3 (Comp) | 4 (Comp) | 5 | 6 (Comp) | 7 (Comp) | 8 | 9 |
| Component I | | | | | | | | |
| Polyol 1 | 502.26 | 473.32 | 470.42 | 445.11 | 493.05 | 482.53 | 486.81 | 468.13 |
| Catalyst | 0.25 | 0.24 | 0.25 | 0.25 | 0.25 | 0.25 | 0.25 | 0.25 |
| Solvent Blend | 199.10 | 205.10 | 132.07 | 132.07 | 179.69 | 157.56 | 180.97 | 159.07 |
| Component II | | | | | | | | |
| Comp. Polyisocyanate 9 | 145.59 | — | — | — | 103.44 | 55.36 | 106.22 | 58.64 |
| Comp. Polyisocyanate 10 | — | — | 255.24 | — | 73.89 | 158.18 | — | — |
| Comp. Polyisocyanate 11 | — | 142.00 | — | — | — | — | — | — |
| Polyisocyanate 1 70% in Solvent Blend | — | — | — | 280.54 | — | — | 75.87 | 167.54 |

TABLE 5

| | Example | | | | | | | |
|---|---|---|---|---|---|---|---|---|
| | 2 (Comp) | 3 (Comp) | 4 (Comp) | 5 | 6 (Comp) | 7 (Comp) | 8 | 9 |
| Polyisocyanate | 9 (Comp) HDI Trimer | 11 (Comp) HDI Trimer/ Allophanate | 10 (Comp) IPDI Trimer | 1 IPDI Trimer/ Allophanate | 67% Comp Polyiso 9/ 33% Comp Polyiso 10 | 33% Comp Polyiso 9/ 67% Comp Polyiso 10 | 67% Comp Polyiso 9/ 33% Polyisocyanate I | 33% Comp Polyiso 9/ 66% Polyisocyanate I |
| Viscosity (sec) | | | | | | | | |
| Initial | 20 | 19 | 29.9 | 18.5 | 21.8 | 25.0 | 19.7 | 19.2 |
| 30 min. | 23.0 | — | 33.5 | 19.3 | 22.4 | 26.3 | 21.1 | 20.3 |
| 60 min. | 23.9 | 21.0 | 37.3 | 19.7 | 23.9 | 28.5 | 22.8 | 20.8 |
| 90 min. | 25.3 | — | 38.7 | 20.0 | 28.8 | 31.3 | 23.5 | 21.8 |
| 120 min. | 26.5 | 24.6 | 42.8 | 20.2 | 30.1 | 33.4 | 23.9 | 22.0 |
| Tack free time | | | | | | | | |
| minutes | 120+ | 210 | 30 | 90 | 90 | 60 | 120+ | 120 |
| Gardener Dry Times (min) | | | | | | | | |
| Set to touch | 60 | 60 | 60 | 90 | 90 | 45 | 90 | 90 |
| Surface dry | 180 | 210 | 135 | 390 | 240 | 130 | 240 | 330 |
| Hard dry | 330 | 270 | 255 | 540 | 310 | 230 | 300 | 750 |
| Mar free | 480 | 600 | 24 hr + | 24 hr + | 680 | 720 | 840 | 24+ |
| Hardness (sec) | | | | | | | | |
| 24 hrs | 112 | 47 | 140 | 84 | 125 | 133 | 99 | 81 |
| 48 hrs | 122 | — | 148 | 109 | 144 | 151 | 122 | 140 |
| 2 weeks | 137 | 112 (1 week) | 182 | 181 | 162 | 171 | 181 | 171 |

By comparing Examples 4 and 5, it is seen that the presence of allophanate groups in Polyisocyanate 1 leads to a 10 second decrease in Zahn viscosity. This is significant because the viscosity of the coating composition from Example 4 is too high for spray applications (which generally require an initial viscosity of 25 seconds or less), while in Example 3 the viscosity is ideal for spraying. This result is surprising because a similar comparison between Examples 2 and 3 (wherein the polyisocyanates are prepared from HDI instead of IPDI) only results in a 1 second decrease in viscosity. Accordingly, the 10 second difference in viscosity becoatings obtained in Examples 4 and 5 were equivalent.

Based on these results it is possible in accordance with the present invention (Example 5) to prepare coating compositions having a very low viscosity which become dust free faster than coating compositions based on polyisocyanates prepared from HDI (Examples 2 and 3) and yet have the same ultimate hardness as coating compositions based on non-allophanate-containing polyisocyanates prepared from IPDI (Example 4).

Blends of the IPDI allophanates according to the invention with conventional polyisocyanates, such as Comparison Polyisocyanate 9, are compared with Comparison Polyisocyanate 10 in Example 6-9. Similar trends are again seen in viscosity, dry times and ultimate hardness.

Examples 10-13—Elevated cure coating compositions

In these examples coating compositions were prepared from two IPDI trimer/allophanates (Polyisocyanates 1 and 6) and from an IPDI trimer (Comparison Polyisocyanate 10). In all examples these polyisocyanates were first blended with either Comparison Polyisocyanate 9 (Examples 10-12) or Comparison Polyisocyanate 11 (Example 13) in a weight ratio of 75:25, based on solids, and then reacted with Polyol 2 at an NCO/OH equivalent ratio of 1.0:1.0. The coating compositions also contained the additives specified in Table 6. Sufficient n-butyl acetate was added to the coating compositions to reduce the viscosity to 20 seconds (Zahn #2 cup, 25° C.). The solids content was measured after the addition of solvent and is reported in Table 6.

The coating compositions were spray applied over a commercial base coat at a dry film thickness of 1.5 mils and baked at about 120° C. for 30 minutes. The properties of the resulting coatings are set forth in Table 7.

TABLE 6

|  | Example | | | |
|---|---|---|---|---|
|  | 10 | 11 | 12 (Comp) | 13 (Comp) |
| Component I |  |  |  |  |
| Polyol 2 | 65.18 | 60.20 | 59.64 | 60.14 |
| Additive 1 | 0.92 | 0.84 | 0.78 | 0.80 |
| Additive 2 | 1.86 | 1.72 | 1.63 | 1.67 |
| Additive 3 | 1.86 | 1.72 | 1.63 | 1.67 |
| n-butyl acetate | 22.40 | 31.3 | 36.75 | 34.83 |
| Component II |  |  |  |  |
| Polyisocyanate 1 - 70% in Aromatic 100 Solvent | 43.18 | — | — | — |
| Polyisocyanate 6 - 70% in Aromatic 100 Solvent | — | 41.32 | — | — |
| Comp. Polyisocyanate 10 | — | — | 39.32 | 41.26 |
| Comp. Polyisocyanate 9* | 14.60 | 13.5 | 10.21 | — |
| Comp. Polyisocyanate 11 | — | — | — | 9.63 |
| Total | 150 | 150 | 150 | 150 |
| Solids (%) | 64.3 | 60 | 56.8 | 58.3 |
| VOC (g/l) | 368 | 408 | 434 | 420 |
| Viscosity (sec) | 20 | 20 | 20 | 20 |

*Present at 90% solids in a 1:1 blend of Aromatic 100 solvent and n-butyl acetate.

TABLE 7

| Example | Polyisocyanate | % Solids | Hardness (sec) | MEK Resistance |
|---|---|---|---|---|
| 10 | 75% Polyisocyanate 1 25% Comp Polyiso 9 | 64.3 | 196 | >100 |
| 11 | 75% Polyisocyanate 6 25% Comp Polyiso 9 | 60 | 190 | >100 |
| 12 (Comp) | 75% Comp Polyiso 10 25% Comp Polyiso 9 | 56.8 | 192 | >100 |
| 13 (Comp) | 75% Comp Polyiso 10 25% Comp Polyiso 11 | 58.3 | 185 | >100 |

With both of the polyisocyanates according to the invention (Examples 10 and 11), it was possible to formulate a sprayable coating composition having a viscosity of 20 seconds at solids content of 64.7% and 60%, respectively. It was necessary to reduce the solids content of the compositions containing Comparison Polyisocyanate 10 (Examples 12 and 13) to 56.8% and 58.3%, respectively, in order to obtain this spray viscosity. This represents a substantial reduction in solvent content.

Also of importance is the evidence for completeness of cure in all systems given by the pendulum hardness and MEK double rub resistance. After cooling to room temperature, tests on all panels demonstrate similar an improvement in either or both of hardness and excellent MEK resistance.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate mixture having an NCO content of 5 to 47% by weight and containing isocyanurate and allophanate groups in a molar ratio of monoisocyanurates to monoallophanates of 10:1 to 1:10 which comprises
   a) catalytically trimerizing a portion of the isocyanate groups of an isocyanate component substantially containing one or more cyclic organic diisocyanates having (cyclo)aliphatically bound isocyanate groups
   b) adding 0.01 to 0.5 moles, per mole of organic diisocyanate, of a monoalcohol containing at least one carbon atom and having a molecular weight of up to 2500 to the organic diisocyanate prior to or during the trimerization reaction of step a) and
   c) terminating the trimerization reaction at the desired degree of trimerization by adding a catalyst poison and/or by thermally deactivating the catalyst.

2. The process of claim 1 wherein said cyclic organic diisocyanate comprises isophorone diisocyanate.

3. The process of claim 1 wherein said monoalcohol comprises a hydrocarbon monoalcohol containing 1 to 20 carbon atoms.

4. The process of claim 2 wherein said monoalcohol comprises a hydrocarbon monoalcohol containing 1 to 20 carbon atoms.

5. The process of claim 1 wherein said monoalcohol comprises 1-butanol.

6. The process of claim 2 wherein said monoalcohol comprises 1-butanol.

7. A polyisocyanate mixture which
   i) has an NCO content of 5 to 47% by weight,
   ii) is prepared from an isocyanate component substantially containing one or more cyclic organic diisocyanates having (cyclo)aliphatically-bound isocyanate groups and
   iii) contains isocyanurate and allophanate groups in a molar ratio of monoisocyanurates to monoallophanates of 10:1 to 1:10, wherein the allophanate groups are formed from urethane groups which are based on the reaction product of an organic diisocyanate having (cyclo)aliphatically bound isocyanate groups and a monoalcohol containing at least one carbon atom and having a molecular weight of up to 2500.

8. The polyisocyanate mixture of claim 7 wherein said cyclic organic diisocyanate comprises isophorone diisocyanate.

9. The polyisocyanate mixture of claim 7 wherein said monoalcohol comprises a hydrocarbon monoalcohol containing 1 to 20 carbon atoms.

10. The polyisocyanate mixture of claim 8 wherein said monoalcohol comprises a hydrocarbon monoalcohol containing 1 to 20 carbon atoms.

11. The polyisocyanate mixture of claim 7 wherein said monoalcohol comprises 1-butanol.

12. The polyisocyanate mixture of claim 8 wherein said monoalcohol comprises 1-butanol.

13. A two-component coating composition comprising the polyisocyanate of claim 7 and a compound containing isocyanate-reactive groups.

* * * * *